United States Patent [19]

Lee et al.

[11] 4,066,667
[45] Jan. 3, 1978

[54] 9-HYDROXY-7,8,9,10-TETRAHYDRO-6H, DIBENZO[B][D] PYRANS AND PYRANONES

[75] Inventors: Cheuk Man Lee, Libertyville; Raymond John Michaels, Mundelein, both of Ill.; Louis Selig Harris, Richmond, Va.

[73] Assignee: Abbott Laboratories, North Chicago, Ill.

[21] Appl. No.: 593,352

[22] Filed: July 7, 1975

[51] Int. Cl.$^2$ .................. C07D 311/78; A61K 31/35; A61K 31/335
[52] U.S. Cl. .................. 260/345.3; 424/279; 424/283; 260/343.21
[58] Field of Search ...................... 260/345.3
[56] References Cited

U.S. PATENT DOCUMENTS 3,507,885  4/1970  Fahrenholtz .............. 260/345.3

OTHER PUBLICATIONS

Petrzilka et al., Helv. Chim. Acta, 57, 121 (1974).

Primary Examiner—Nicky Chan
Attorney, Agent, or Firm—Gildo E. Fato; Robert L. Niblack

[57] ABSTRACT

Compounds of the formula

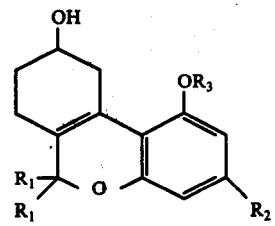

wherein $R_1$ is methyl or $R_1R_1$ is oxygen; $R_2$ is alkyl or halogen substituted phenyl alkyl; and $R_3$ is hydrogen, loweralkyl, loweralkenyl or loweralkynyl.

The compounds of this invention are useful as analgesics and tranquilizers.

9 Claims, No Drawings

9-HYDROXY-7,8,9,10-TETRAHYDRO-6H, DIBENZO[B][D] PYRANS AND PYRANONES

DETAILED DESCRIPTION OF THE INVENTION

This invention relates to benzopyrans and more particularly to 9-hydroxy-7, 8, 9, 10-tetrahydro-6H-dibenzo [b] [d] pyrans and pyranones represented by the formula

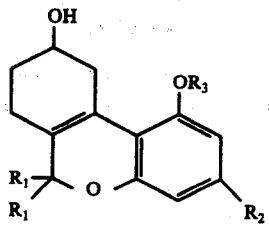

wherein $R_1$ is methyl or $R_1R_1$ is oxygen; $R_2$ is alkyl or halogen substituted phenyl alkyl; and $R_3$ is hydrogen, loweralkyl, loweralkenyl or loweralkynyl.

As used herein the term "loweralkyl" refers to $C_1-C_6$ straight or branched chain alkylene groups including methyl, ethyl, n-propyl, iso-propyl, n-butyl, sec-butyl, tert-butyl, n-pentyl, iso-pentyl, neo-pentyl, n-hexyl and the like.

The term "alkyl" refers to straight and branched chain alkyl radicals having from 1 to 20 carbons atoms such as methyl, n-amyl, 3-methyl-2-octyl, 2-nonyl,2-eicosanyl and the like.

The term "halogen" includes chlorine, fluorine, bromine and iodine.

The term "loweralkenyl" refers to straight and branched chain $C_2-C_6$ alkyl radicals from which a hydrogen atom has been removed from each of two adjacent carbon atoms to produce ethylenic unsaturation; e.g., vinyl, allyl, methallyl, 1-pentenyl and the like.

The term "loweralkynyl" refers to $C_2-C_6$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like groups.

The present compounds are prepared according to the following reaction scheme:

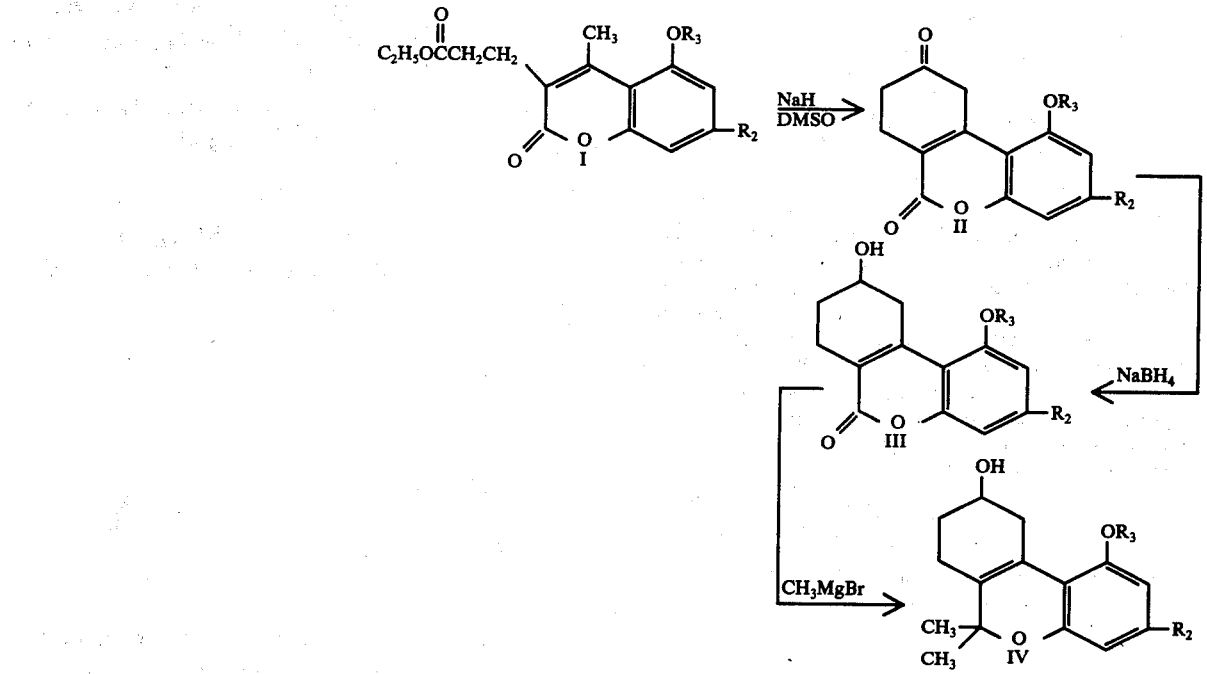

In the reaction illustrated above, the starting material, 5-hydroxy-4-methyl-7-alkylcoumarin-3-propionate (I), is obtained by reaction of 5-alkylresorcinol with dialkyl β-acetylglutarate in the presence of phosphorus oxychloride. The coumarin (I) is then cyclized to 1-hydroxy-3-alkyl-6, 9-dioxo-7, 8, 9, 10-tetrahydro-6H-dibenzo [b] [d] pyran (II) with sodium hydride in dimethyl sulfoxide, which, in turn, is reduced with sodium borohydride to 1, 9-dihydroxy-3-alkyl-6-oxo-7, 8, 9, 10-tetrahydro-6H-dibenzo [b] [d] pyran (III). Compound (III) is then converted to 1, 9-dihydroxy-6, 6-dimethyl-3-alkyl-7, 8, 9, 10-tetrahydro-6H-dibenzo [b] [d] pyran (IV) with methyl magnesium bromide.

The compounds of this invention are useful as analgesic agents and tranquilizers. The compounds are effective at dosages generally from 1 to 10 mg./kg. of body weight daily. The analgesic activity was established in the standard mouse writhing test [Whittle, Brit. J. Pharmacol., 22,296 (1964)] and confirmed in the hot plate assay [Woolfe, G. and MacDonald, A. D., J. Pharmacol. Exper. Therap., 80,300, (1944)] and the rat tail flick test.

The following examples further describe and illustrate the present invention.

EXAMPLE 1

Ethyl 5-Hydroxy-4-Methyl-7-(3-Methyl-2-Octyl)Coumarin-3-Propionate

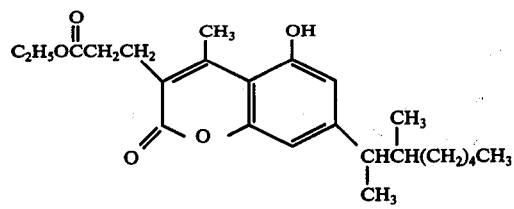

A mixture of 262 g. (1.109 mole) of 5-(3-methyl-2-octyl)resorcinol, 283 g. (1.23 mole) of diethyl α-acetylglutarate, and 170 g. (1.11 mole) of phorphorus oxychloride protected from atmospheric mositure is stirred at room temperature for 12 days. The mixture is taken up in benzene-ether and the solution is washed several times with water, aqueous sodium bicarbonate, water and dried over anhydrous magnesium sulfate. After removal of the solvent, 441 g. of an oil is obtained, which solidifies on standing.

EXAMPLE 2

Ethyl 7-[5-(p-Fluorophenyl)-2-Pentyl]-5-Hydroxy-4-Methyl-coumarin-3-Propionate

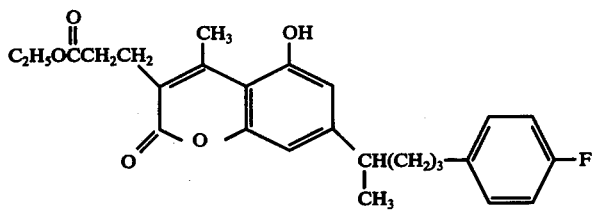

Ethyl 7-[5-(p-fluorophenyl)-2-pentyl]-5-hydroxy-4-methylcoumarin-3-propionate is prepared by reaction of 5-[5-(p-fluorophenyl)-2-pentyl]resorcinol, diethyl α-acetylglutarate, and phosphorus oxychloride according to the method of Example 1.

EXAMPLE 3

1-Hydroxy-3-(3-Methyl-2-Octyl)-6, 9-Dioxo-7, 8, 9, 10-Tetrahydro-6H-Dibenzo [b] [d] Pyran

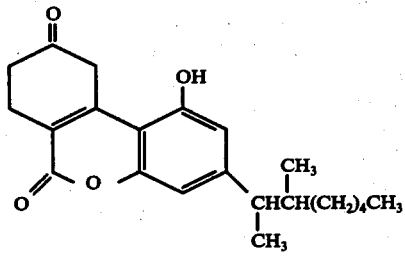

To a stirred solution of 43.8 g. (0.1088 mole) of ethyl 5-hydroxy-4-methyl-7-(3-methyl-2-octyl)coumarin-3-propionate in 325 ml. of dry reagent grade dimethyl sulfoxide is added, portionwise, 19.6 g. (0.466 mole) of 57% sodium hydride in mineral oil. The mixture is stirred at room temperature overnight and poured into 1200 ml. of ice and water. The dark solution is extracted twice with ether to remove the mineral oil. Concentrated hydrochloric acid (75 ml.) is added to the stirred aqueous solution and after 1 hour of stirring, the slurry is filtered and the solid is washed well with water. The wet filter cake is heated on the steam bath with excess concentrated sodium bicarbonate solution and is filtered. The solid is washed well with water and recrystallized from acetonitrile to give the pure product; m.p. 150-151°.

Analysis Calcd. for $C_{22}H_{28}O_4$: C, 74.13; H, 7.92; O, 17.95; Found: C, 73.70; H, 7.98; O, 18.34

EXAMPLE 4

3-[5-(p-Fluorophenyl)-2-Pentyl]-1-Hydroxy-6, 9-Dioxo-7, 8, 9, 10-Tetrahydro-6H-Dibenzo [b] [d] Pyran

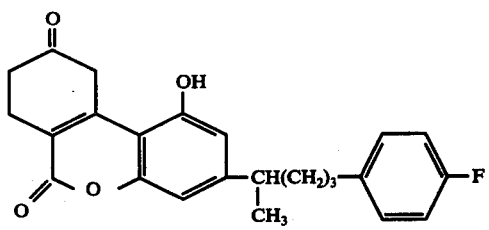

3-[5-(p-Fluorophenyl)-2-pentyl]-1-hydroxy-6, 9-dioxo-7, 8, 9, 10-tetrahydro-6H-dibenzo [b] [d] pyran is prepared by reacting ethyl 7-[5-(p-fluorophenyl)-2-pentyl]-5-hydroxy-4-methylcoumarin-3-propionate with sodium hydride in dimethyl sulfoxide according to the method of Example 3; m.p. 174°-176°.

EXAMPLE 5

1, 9-Dihydroxy-3-(3-Methyl-2-Octyl)-6-Oxo-7, 8, 9, 10-Tetrahydro-6H-Dibenzo [b] [d] Pyran

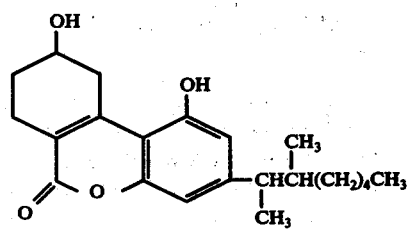

A mixture of 3.56 g. (0.01 mole) of 1-hydroxy-3-(3-methyl-2-octyl)-6, 9-dioxo-7, 8, 9, 10-tetrahydro-6H-dibenzo [b] [d] pyran, 3.8 g. (0.1 mole) of sodium borohydride, 80 ml. of tetrahydrofuran, 5 ml. of 5% sodium hydroxide solution and 5 ml. of water is stirred and refluxed for 20 hours. With addition of 40 ml. of water, the mixture is refluxed for another one-half hour. The tetrahydrofuran is evaporated in vacuo, and the residue is extracted with chloroform. After removal of the solvent, an amorphous solid is obtained; m.p. 88°-90°.

Analysis Calcd. for $C_{22}H_{30}O_4$: C, 73.71; H, 8.44; O, 17.85; Found: C, 73.49; H, 8.60; O, 17.97

EXAMPLE 6

3-[5-(p-Fluorophenyl)-2-Pentyl]-1, 9-Dihydroxy-6-Oxo-7, 8, 9, 10-Tetrahydro-6H-Dibenzo [b] [d] Pyran

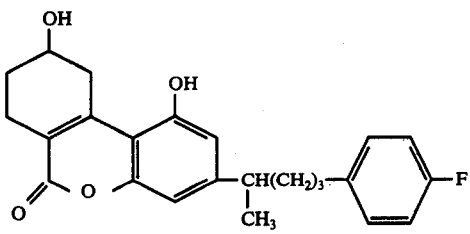

A mixture of 11.3 g. (0.0286 mole) of 3-[5-(p-fluorophenyl-2-pentyl]-1-hydroxy-6, 9-dioxo-7, 8, 9, 10-tetrahydro-6H-dibenzo [b] [d] pyran, 10.9 g. (0.286 mole) of sodium borohydride, 200 ml. of tetrahydrofuran, 10 ml. of 5% sodium hydride solution and 10 ml. of water is stirred and refluxed for 19 hours. With addition of 60 ml. of water, the mixture is refluxed for another one-half hour. The tetrahydrofuran is evaporated in vacuo, and the residue is treated with water, acidified with dilute hydrochloric acid, and extracted with chloroform. The chloroform solution is dried over magnesium sulfate, and evaporated in vacuo. The residue is purified by chromatography on a Florisil® column, using methanol/chloroform solvent mixtures to give the pure product; m.p. 87°–92°.

Analysis Calcd. for $C_{24}H_{25}FO_4$: C, 72.71; H, 6.36; Found: C, 72.98; H, 6.36

EXAMPLE 7

1, 9-Dihydroxy-6, 6-Dimethyl-3-(3-Methyl-2-Octyl)-7, 8, 9, 10-Tetrahydro-6H-Dibenzo [b] [d] Pyran

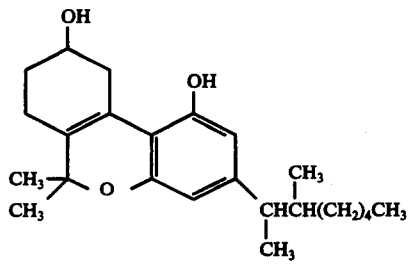

A solution of 3.4 g. (0.00948 mole) of 1,9-dihydroxy-3-(3-methyl-2-octyl)-6-oxo-7, 8, 9, 10-tetrahydro-6H-dibenzo [b] [d] pyran in 75 ml. of ether is added dropwise to a stirred solution of 31.6 ml. (0.0948 mole) of methyl magnesium bromide 3/M in ether. The mixture is stirred and refluxed for 20 hours. The complex is decomposed by addition of water, followed by ammonium chloride solution. The ether solution is decanted and the gelatinous inorganic salt is washed well with ether. The combined ether solution is dried and evaporated in vacuo. The residue is dissolved in benzene and refluxed with a few crystals of p-toluenesulfonic acid monohydrate for one-half hour, with a Dean-Stark trap to remove the water formed. After removal of the solvent, the residue is chromatographed on a Florisil® (60-100/mesh) column, using graded methanol/chloroform solvent mixtures to yield the pure product.

Analysis Calcd. for $C_{24}H_{36}O_3$: C, 77.37; H, 9.74; O, 12.89; Found: C, 77.47; H, 9.80; O, 13.44

EXAMPLE 8

3-[5-(p-Fluorophenyl)-2-Pentyl]-1, 9-Dihydroxy-6, 6-Dimethyl-7, 8, 9, 10-Tetrahydro-6H-Dibenzo [b] [d] Pyran

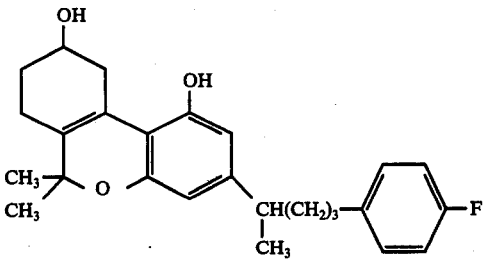

3-[5-(p-Fluorophenyl)-2-pentyl]-1, 9-dihydroxy-6, 6-dimethyl-7, 8, 9, 10-tetrahydro-6H-dibenzo [b] [d] pyran is prepared by reacting 3-[5-(p-fluorophenyl)-2-pentyl]-1, 9-dihydroxy-6-oxo-7, 8, 9, 10-tetrahydro-6H-dibenzo-[b] [d] pyran with methyl magnesium bromide according to the method of Example 7. The crude product is purified by chromatography on a Florisil® column, using chloroform as eluant.

Analysis Calcd. for $C_{26}H_{31}FO_3$: C, 76.07; H, 7.61; Found: C, 75.57; H, 7.59

EXAMPLE 9

9-Hydroxy-1-Methoxy-3-(3-Methyl-2-Octyl)-6-Oxo-7, 8, 9, 10-Tetrahydro-6H-Dibenzo [b] [d] Pyran

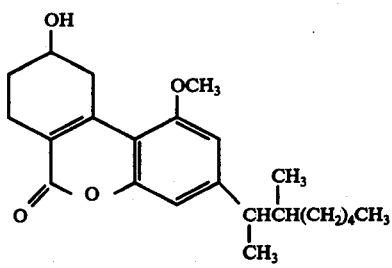

A solution of 8.0 g. (0.0224 mole) of 1-hydroxy-3-(3-methyl-2-octyl)-6, 9-dioxo-7, 8, 9, 10tetrahydro-6H-dibenzo [b] [d] pyran in 50 ml. of dimethyl formamide is added dropwise to a stirred suspension of 1.7 g. (0.04 mole) of sodium hydride (57% in mineral oil). The mixture is stirred and heated in an oil bath at 80° for 2 hours. After cooling, 0.83 g. (0.005 mole) of potassium iodide is added, followed by dropwise addition of 5.9 g. (0.042 mole) of methyl iodide. The mixture is stirred at room temperature for 48 hours. After addition of 100 ml. of water, the mixture is extracted with ether. The ether extract is washed with water, dried, and evaporated in vacuo. The residue is reduced with sodium borohydride according to Example 5. The crude produce is purified by chromatography on a Florisil® column, using graded methanol/chloroform solvent mixtures.

EXAMPLE 10

9-Hydroxy-1-Methoxy-6,
6-Dimethyl-3-(3-Methyl-2-Octyl)-7, 8, 9,
10-Tetrahydro-6H-Dibenzo [b] [d] Pyran

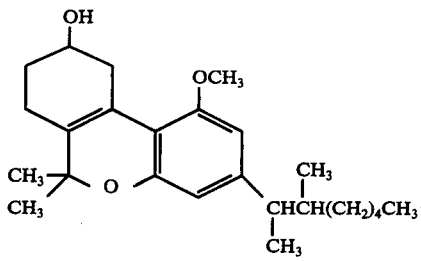

9-Hydroxy-1-methoxy-6, 6-dimethyl-3-(3-methyl-2-octyl)-7, 8, 9, 10-tetrahydro-6H-dibenzo [b] [d] pyran is prepared by reacting 9-hydroxy-1-methoxy-3-(3-methyl-2-octyl)-6-oxo-7, 8, 9, 10-tetrahydro-6H-dibenzo [b] [d] pyran with methyl magnesium bromide according to the method of Example 7. The crude product is purified by chromatography on a Florisil ® column, using chloroform as eluant.

Analysis Calcd. for $C_{25}H_{38}O_3$: C, 77.67; H, 9.91; O, 12.42; Found: C, 77.43; H, 10.05; O, 12.21

EXAMPLE 11

1-Allyloxy-9-Hydroxy-3-(3-Methyl-2-Octyl)-6-Oxo-7, 8, 9, 10-Tetrahydro-6H-Dibenzo [b] [d] Pyran

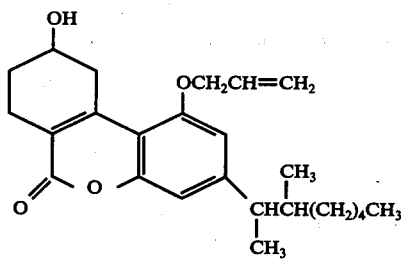

1-Allyloxy-9-hydroxy-3-(3-methyl-2-octyl)-6-oxo-7, 8, 9, 10-tetrahydro-6H-dibenzo [b] [d] pyran is prepared by reacting 1-hydroxy-3-(3-methyl-2-octyl)-6, 9-dioxo-7, 8, 9, 10-tetrahydro-6H-dibenzo [b] [d] pyran with allyl bromide and reducing the product with sodium borohydride according to the method of Example 9.

EXAMPLE 12

9-Hydroxy-3-(3-Methyl-2-Octyl)-1-(2-Propynyloxy)-6-Oxo-7, 8, 9, 10-Tetrahydro-6H-Dibenzo [b] [d] Pyran

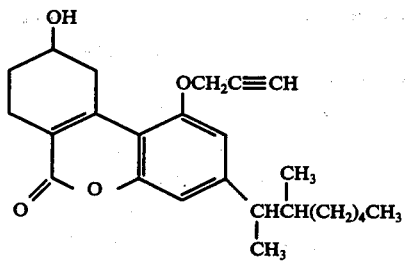

9-Hydroxy-3-(3-methyl-2-octyl)-1-(2-propynyloxy)-6-oxo-7, 8, 9, 10-tetrahydro-6H-dibenzo [b] [d] pyran is prepared by reacting 1-hydroxy-3-(3-methyl-2-octyl)-6, 9-dioxo-7, 8, 9, 10-tetrahydro-6H-dibenzo [b] [d] pyran with 2-propynyl bromide and reducing the product with sodium borohydride according to the method of Example 9.

EXAMPLE 13

1-Allyloxy-9-Hydroxy-6,
6-Dimethyl-3-(3-Methyl-2-Octyl)-7, 8, 9,
10-Tetrahydro-6H-Dibenzo [b] [d] Pyran

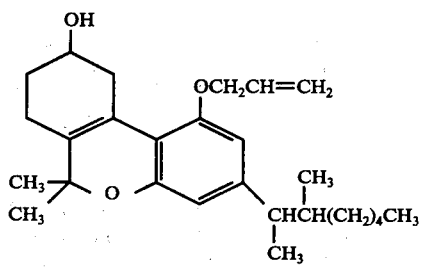

1-Allyloxy-9-hydroxy-6, 6-dimethyl-3-(3-methyl-2-octyl)-7, 8, 9, 10-tetrahydro-6H-dibenzo [b] [d] pyran is prepared by reacting 1-allyloxy-9-hydroxy-3-(3-methyl-2-octyl)-6-oxo-7, 8, 9, 10-tetrahydro-6H-dibenzo [b] [d] pyran with methyl magnesium bromide according to the method of Example 10.

EXAMPLE 14

9-Hydroxy-6,
6-Dimethyl-3-(3-Methyl-2-Octyl)-1-(2-Propynyloxy)-7, 8, 9, 10-Tetrahydro-6H-Dibenzo [b] [d] Pyran

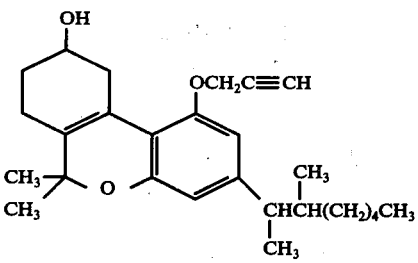

9-Hydroxy-6, 6-dimethyl-3-(3-methyl-2-octyl)-1-(2-propynyloxy)-7, 8, 9, 10-tetrahydro-6H-dibenzo [b] [d] pyran is prepared by reacting 9-hydroxy-3-(3-methyl-2-octyl)-1-(2-propynyloxy)-6-oxo-7, 8, 9, 10-tetrahydro-6H-dibenzo [b] [d] pyran with methyl magnesium bromide according to the method of Example 10.

The present invention includes within its scope, pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ester oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment.

We claim:

1. A compound of the formula

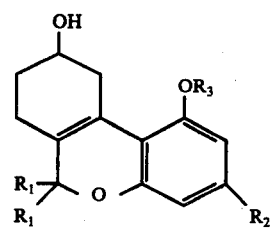

wherein $R_1$ is methyl, $R_2$ is $C_1$–$C_{20}$ alkyl and $R_3$ is hydrogen, loweralkyl, $C_2$–$C_6$ alkenyl or $C_2$–$C_6$ alkynyl.

2. A compound in accordance with claim 1, wherein each $R_1$ is methyl, $R_2$ is $C_1$–$C_{20}$ alkyl, and $R_3$ is hydrogen.

3. A compound in accordance with claim 2, 1, 9-dihydroxy-6, 6-dimethyl-3-(3-methyl-2-octyl)-7, 8, 9, 10-tetrahydro-6H-dibenzo [b] [d] pyran.

4. A compound in accordance with claim 1, wherein each $R_1$ is methyl, $R_2$ is alkyl, and $R_3$ is $CH_3$.

5. A compound in accordance with claim 4, 9-hydroxy-1-methoxy-6, 6-dimethyl-3-(3-methyl-2-octyl)-7, 8, 9, 10-tetrahydro-6H-dibenzo [b] [d] pyran.

6. A compound in accordance with claim 1, wherein each $R_1$ is methyl, $R_2$ is alkyl, and $R_3$ is $C_2$–$C_6$ alkenyl.

7. A compound in accordance with claim 6, 1-allyloxy-9-hydroxy-6, 6-dimethyl-3-(3-methyl-2-octyl)-7, 8, 9, 10-tetrahydro-6H-dibenzo [b] [d] pyran.

8. A compound in accordance with claim 1, wherein each $R_1$ is methyl, $R_2$ is alkyl, and $R_3$ is $C_2$–$C_6$ alkynyl.

9. A compound in accordance with claim 8, 9-hydroxy-6, 6-dimethyl-3-(3-methyl-2-octyl)-1-(2-propynyloxy)-7, 8, 9, 10-tetrahydro-6H-dibenzo [b] [d] pyran.

UNITED STATES PATENT OFFICE
CERTIFICATE OF CORRECTION

PATENT NO. : 4,066,667
DATED : January 3, 1978
INVENTOR(S) : Cheuk Man Lee, Raymond John Michaels, Louis Selig Harris It is certified that error appears in the above-identified patent and that said Letters Patent are hereby corrected as shown below:

On the front page, Assignee should read:

"Sharps Associates, Cambridge, Mass."

instead of:

"Abbott Laboratories, North Chicago, Ill."

Signed and Sealed this

Tenth Day of April 1979

[SEAL]

Attest:

RUTH C. MASON
Attesting Officer

DONALD W. BANNER
Commissioner of Patents and Trademarks